US008343466B2

United States Patent
Takagi et al.

(10) Patent No.: US 8,343,466 B2
(45) Date of Patent: Jan. 1, 2013

(54) HYDROGEL PARTICLES

(75) Inventors: Michiya Takagi, Wakayama (JP); Kimikazu Fukuda, Wakayama (JP); Koji Mine, Wakayama (JP); Keigo Kajiwara, Tokyo (JP); Yoko Nakajima, Tokyo (JP); Yukio Inomata, Tokyo (JP)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 13/131,770

(22) PCT Filed: Nov. 19, 2009

(86) PCT No.: PCT/JP2009/006248
§ 371 (c)(1),
(2), (4) Date: May 27, 2011

(87) PCT Pub. No.: WO2010/061556
PCT Pub. Date: Jun. 3, 2010

(65) Prior Publication Data
US 2011/0236446 A1 Sep. 29, 2011

(30) Foreign Application Priority Data
Nov. 28, 2008 (JP) .................................. 2008-304996

(51) Int. Cl.
*A61K 8/04* (2006.01)
*A61K 8/29* (2006.01)
*A61K 8/34* (2006.01)
*A61K 8/92* (2006.01)
*A61Q 17/04* (2006.01)
*A61Q 1/02* (2006.01)

(52) U.S. Cl. ........................... 424/59; 424/617; 424/401

(58) Field of Classification Search .................. None
See application file for complete search history.

(56) References Cited

U.S. PATENT DOCUMENTS

| 5,344,650 | A  | 9/1994  | Otsuka et al. |
| 6,749,837 | B1 | 6/2004  | Samain et al. |
| 6,841,163 | B2 | 1/2005  | Omura et al. |
| 2002/0034525 | A1 | 3/2002  | Sakai et al. |
| 2004/0241126 | A1 | 12/2004 | Sakuta |
| 2005/0008600 | A1 | 1/2005  | Nakanishi et al. |
| 2009/0155323 | A1 | 6/2009  | Sakai et al. |
| 2010/0008869 | A1 | 1/2010  | Takagi et al. |
| 2010/0015186 | A1 | 1/2010  | Takagi et al. |

FOREIGN PATENT DOCUMENTS

| EP | 1972325 A1 * | 9/2008 |
| JP | 2002 20228 | 1/2002 |
| JP | 2002 159838 | 6/2002 |
| JP | 2004 346046 | 12/2004 |
| JP | 2005 42097 | 2/2005 |
| JP | 2008 19195 | 1/2008 |
| WO | WO 2007066635 A1 * | 6/2007 |

OTHER PUBLICATIONS

International Preliminary Report and Writen Opinion issued Jul. 14, 2011 in PCT/JP2009/006248.
International Search Report issued Feb. 23, 2010 in PCT/JP09/06248 filed Nov. 19, 2009.
Office Action issued Aug. 8, 2012, in China Patent Application No. 200980147726.5 (with English-language Translation).

* cited by examiner

*Primary Examiner* — Daniel Sullivan
*Assistant Examiner* — Peter Anthopolos
(74) *Attorney, Agent, or Firm* — Oblon, Spivak, McClelland, Maier & Neustadt, L.L.P.

(57) ABSTRACT

Hydrogel particles include a continuous phase portion of non-crosslinked hydrogel and disperse phase portions dispersed in the continuous phase portion. Each of the disperse phase portions contains a solid oil and a liquid oil as an oil component, and titanium oxide particles dispersed therein. The solid oil of the oil component contains a higher alcohol and a solid paraffin, and the content of the solid oil in the disperse phase portion is 1 to 12 mass %. The hydrogel particles have a volume-average particle diameter of 10 to 300 μm.

13 Claims, No Drawings

HYDROGEL PARTICLES

CROSS REFERENCES TO RELATED APPLICATIONS

This application is a 371 of International Patent Application No. PCT/JP2009/006248, filed on Nov. 19, 2009, and claims priority to Japanese Patent Application No. 2008-304996, filed on Nov. 28, 2008.

TECHNICAL FIELD

The present invention relates to hydrogel particles in which disperse phase portions containing an oil component are dispersed in a continuous phase portion of non-crosslinked hydrogel, and UV-shielding cosmetic products containing the hydrogel particles.

BACKGROUND ART

In the fields of cosmetic products, drugs, quasi drugs, food products and the like, applications of hydrogel particles in which a large number of disperse phase portions containing an oil component are dispersed in a continuous phase portion of non-crosslinked hydrogel have been studied.

Patent Document 1 describes, as the hydrogel particles, ones in which the oil component contains a solid oil and/or a liquid oil.

Patent Document 2 describes, as the hydrogel particles, ones in which the disperse phase portions are liquid phase containing the oil component, and zinc oxide particles and titanium oxide particles, which have a UV-shielding property, are dispersed in the disperse phase portions.

Patent Document 3 describes, as the hydrogel particles, ones in which the disperse phase portions are solid phase containing the oil component, and zinc oxide particles, which have a UV-shielding property, are dispersed in the disperse phase portions. According to the hydrogel particles, the disperse phase portions in which the zinc oxide particles are dispersed are solid phase, and therefore, the zinc oxide particles are immobilized and are stably present in the disperse phase portions. Therefore, for example, when the hydrogel particles are applied to a cosmetic product or the like, it is possible to avoid a problem that zinc oxide particles leak out of the hydrogel particles and react with other ingredients.

CITATION LIST

Patent Document

PATENT DOCUMENT 1: Japanese Patent Publication No. 2002-159838
PATENT DOCUMENT 2: Japanese Patent Publication No. 2002-20228
PATENT DOCUMENT 3: Japanese Patent Publication No. 2007-153835

SUMMARY OF THE INVENTION

Hydrogel particles according to the present invention include a continuous phase portion of non-crosslinked hydrogel and disperse phase portions dispersed in the continuous phase portion. Each of the disperse phase portions contains a solid oil and a liquid oil as an oil component, and titanium oxide particles dispersed therein. The solid oil of the oil component contains a higher alcohol and a solid paraffin, and the content of the solid oil in the oil component is 1 to 12 mass %. The hydrogel particles have a volume-average particle diameter of 10 to 300 μm.

A UV-shielding cosmetic product according to the present invention contains the hydrogel particles of the present invention.

DESCRIPTION OF EMBODIMENTS

Embodiments will be described hereinafter.

(Hydrogel Particles)

Hydrogel particles of this embodiment include a continuous phase portion of non-crosslinked hydrogel and a large number of disperse phase portions dispersed in the continuous phase portion. Each disperse phase portion contains a solid oil and a liquid oil as an oil component, and contains titanium oxide particles dispersed therein. Also, the solid oil of the oil component contains a higher alcohol and a solid paraffin, and the content of the solid oil in the oil component is 1 to 12 mass %. The hydrogel particles are useful for applications in the fields of cosmetic products, drugs, quasi drugs, food products and the like.

The term "hydrogel particle(s)" as referred to in this application means one or more particles of hydrogel in which disperse phase portions containing an oil component are dispersed. It should be noted that the concept of the "hydrogel particle" does not include a capsule composed of a concentric outer layer (shell) and inner layer (core). The term "hydrogel" as referred to in this application means gel which is formed from a gel source using water as solvent.

The volume-average particle diameter of the hydrogel particles is 10 to 300 μm, and in terms of appearance and productivity, more preferably 10 to 250 μm, and especially preferably 30 to 150 μm. Note that the volume-average particle diameter of the hydrogel particles can be measured by a laser diffraction scattering method using a laser diffraction/scattering particle size distribution analyzer (e.g., Model No. LA-910 manufactured by HORIBA, Ltd.).

The shape of the hydrogel particle is not particularly limited and is preferably the shape of a body of revolution which is composed of a curved surface. The "body of revolution which is composed of a curved surface" refers to a three-dimensional body defined by rotating a closed plane formed by a continuous curve and a virtual axis about the virtual axis, excluding three-dimensional bodies having a flat surface, such as triangular pyramids, cylinders and the like. In terms of aesthetic appearance, the shape of the hydrogel particle is more preferably spherical.

The hydrogel particles of this embodiment include a continuous phase portion of non-crosslinked hydrogel.

In terms of prevention of collapse during washing of the hydrogel particles and blending of the hydrogel particles into cosmetic products or the like, the content of the continuous phase portion in the hydrogel particle is preferably 30 to 99 mass %, more preferably 30 to 80 mass %.

The term "non-crosslinked hydrogel" as referred to in this application means a product of gelation caused by thermally reversible sol-gel transition. The non-crosslinked hydrogel generally preferably has a dissolution temperature in water of 75° C. or more, more preferably 75 to 90° C. The non-crosslinked hydrogel also preferably has a gelation temperature of 30 to 45° C. when cooled after being dissolved in water.

The continuous phase portion is non-crosslinked hydrogel which contains a gel source and water as an aqueous component.

Examples of the gel source include agar, carrageenan, gelatin and the like. The gel source may contain one of these examples or may contain more than one of these examples. It should be noted that, as the gel source, agar is preferable among these examples. In terms of a feel in use of cosmetic products or the like containing the hydrogel particles, the jelly strength of the non-crosslinked hydrogel is preferably 147 kPa (1500 g/cm$^2$) or lower, more preferably 19.6 kPa (200 g/cm$^2$) to 127 kPa (1300 g/cm$^2$). The jelly strength can be determined using the Nikkansuishiki method, which is specified as follows. Initially, a 1.5 mass % aqueous solution of the gel source is prepared. The aqueous solution is allowed to stand at 20° C. for 15 hours to obtain a gel product. A load is applied to the gel product using a Nikkansuishiki jelly strength measuring apparatus (manufactured by Kabushiki Kaisha KIYA SEISAKUSHO). The gel strength is represented by the maximum mass (g) per unit surface area (1 cm$^2$) when the gel product withstands the load for 20 seconds at 20° C.

In terms of good feel in use of cosmetic products or the like containing the hydrogel particles and in terms of prevention of collapse during washing of the hydrogel particles and blending of the hydrogel particles into cosmetic products or the like, the content of the gel source in the hydrogel particle is preferably 0.1 mass % or more, more preferably 0.3 mass % or more, even more preferably 0.4 mass % or more, and especially preferably 0.5 mass % or more. In terms of good feel in use of cosmetic products or the like containing the hydrogel particles and in terms of prevention of collapse during washing of the hydrogel particles and blending of the hydrogel particles into cosmetic products or the like, the content of the gel source in the hydrogel particle is preferably 8.0 mass % or less, more preferably 7.0 mass % or less, even more preferably 6.0 mass %, and especially preferably 5.0 mass %.

The hydrogel particles of this embodiment include a plurality of disperse phase portions dispersed in the continuous phase portion.

In terms of prevention of collapse during washing of the hydrogel particles and blending of the hydrogel particles into cosmetic products or the like, the content of the disperse phase portions in the hydrogel particle is preferably 1 to 70 mass %, more preferably 7.5 to 70 mass %, even more preferably 10 to 70 mass %, and especially preferably 20 to 60 mass %.

The volume-average particle diameter of the disperse phase portions is preferably 1/10 or less of the volume-average particle diameter of the hydrogel particles. Specifically, in terms of smooth spreadability over the human skin of cosmetic products or the like containing the hydrogel particles, the volume-average particle diameter of the disperse phase portions is preferably 100 μm or less, more preferably 50 μm or less, and especially preferably 20 μm or less. In terms of compatibility with the human skin of cosmetic products or the like containing the hydrogel particles, the volume-average particle diameter of the disperse phase portions is preferably 0.01 μm or more, more preferably 1 μm or more, even more preferably 4 μm or more, especially preferably 5 μm or more, and most preferably 10 μm or more. Thus, the volume-average particle diameter of the disperse phase portions is preferably 0.01 to 100 μm, more preferably 1 to 100 μm, even more preferably 4 to 100 μm, especially preferably 5 to 50 μm, and most preferably 5 to 20 μm. The volume-average particle diameter of the disperse phase portions can be measured in a dispersion before particle formation using a laser diffraction/scattering particle size distribution analyzer (e.g., Model No. LA-910 manufactured by HORIBA, Ltd.).

In the hydrogel particles of this embodiment, each disperse phase portion contains an oil component.

In terms of good feel in use of cosmetic products or the like containing the hydrogel particles, the total content of the oil component in all the disperse phase portions is preferably 1 to 99 mass %, more preferably 50 to 99 mass %.

In terms of good feel in use of cosmetic products or the like containing the hydrogel particles and in terms of prevention of collapse during washing of the hydrogel particles and blending of the hydrogel particles into cosmetic products or the like, the total content of the oil component in the hydrogel particle is preferably 0.01 to 60 mass %, more preferably 7.5 to 50 mass %, and even more preferably 10 to 40 mass %.

The melting point of the oil component is preferably 40 to 90° C., more preferably 50 to 80° C. The melting point of the oil component can be measured by Differential Scanning Calorimetry (DSC). The melting points of a solid oil and a liquid oil (described below) can also be measured by DSC.

The oil component contains solid oil and liquid oil.

The term "solid oil" as is referred to in this application refers to an oil component having a melting point of 35° C. or more. The term "liquid oil" as is referred to in this application refers to an oil component having a melting point of less than 35° C.

The content of the solid oil in the oil component is 1 to 12 mass %, preferably 2 to 10 mass %, and more preferably 4 to 10 mass %.

The melting point of the overall solid oil contained in the oil component is preferably 35° C. or more, more preferably 40 to 120° C.

The solid oil contains a solid higher alcohol and a solid paraffin. As a result, it is considered that, in the hydrogel particles of this embodiment, a sealing film made of the solid oil is formed on a surface of the disperse phase portion, whereby even a small amount of the solid oil allows the titanium oxide particles to be stably present in the disperse phase portion. Thus, by using the solid oil containing a solid higher alcohol and a solid paraffin, when the hydrogel particles containing the solid oil is applied to a cosmetic product or the like, it is possible to avoid a problem that titanium oxide particles leak out of the hydrogel particles and react with other ingredients, and also a problem, such as poor spreadability when being applied or a sticky feel after being applied.

Preferable examples of the solid higher alcohol include solid higher alcohols with 14 to 32 carbon atoms, such as myristyl alcohol, cetyl alcohol, cetostearyl alcohol, stearyl alcohol, 2-octyldodecanol, arachidyl alcohol, behenyl alcohol and the like. The solid higher alcohol may contain only one material or may contain a plurality of materials. Among these examples, the solid higher alcohol more preferably contains cetyl alcohol, stearyl alcohol, arachidyl alcohol, and behenyl alcohol, which have 14 to 22 carbon atoms. Even more preferably, the solid higher alcohol contains two or more of these higher alcohols. The content of the higher alcohol in the oil component is preferably 1 to 10 mass %, more preferably 2 to 6 mass %.

Examples of the solid paraffin include paraffin waxes and microcrystalline waxes listed in JIS K 2235, ceresine, soft waxes, and paraffins listed in the Japanese Pharmacopoeia, and the like. The solid paraffin may contain only one material or may contain a plurality of materials. The content of the solid paraffin in the oil component is preferably 1 to 10 mass %, more preferably 2 to 6 mass %.

Examples of other solid oils which can be contained in the oil component include solid ceramides, solid sphingolipids, vaselines, solid silicones, solid oils, solid perfumes and the like.

The content of the liquid oil in the disperse phase portion is preferably 40 to 90 mass %, more preferably 50 to 80 mass %.

The melting point of the overall liquid oil contained in the oil component is preferably less than 35° C.

Examples of the liquid oil include liquid skin protecting agents, liquid oils, liquid perfumes and the like. The liquid oil may contain only one material or may contain a plurality of materials.

The liquid skin protecting agent is a component for softening or smoothing the human skin for the purpose of preventing skin surface roughening. Examples of the liquid skin protecting agent include: liquid fats and oils, such as liquid paraffins, liquid ester oils, liquid higher alcohols, liquid squalanes, liquid glycerides and the like; liquid ceramides, such as cetyloxypropyl glyceryl methoxypropyl myristamide and the like; and liquid sphingolipids, such as 1-(2-hydroxyethylamino)-3-isostearyloxy-2-propanol and the like. The liquid skin protecting agent may contain only one material or may contain a plurality of materials. The content of the liquid skin protecting agent in the oil component is preferably 10 to 99 mass %, more preferably 20 to 95 mass %.

Examples of the other types of the liquid oils include liquid hydrocarbon oils, liquid vegetable oils, liquid fatty acids; liquid fats and oils, such as liquid ethylene glycol di-fatty acid esters (fatty acid having 12 to 36 carbon atoms), liquid dialkyl ethers (with 12 to 36 carbon atoms) and the like; and liquid silicones. Examples of the liquid vegetable oils include soybean oil, coconut oil, palm kernel oil, linseed oil, cottonseed oil, colza oil, tung oil, castor oil and the like. Examples of the liquid fatty acids include oleic acid, caprylic acid and the like. The liquid silicones may be any one having a silanol structure. Examples of the liquid silicones include methylpolysiloxane, methylphenylsiloxane, octamethylcyclotetrasiloxane, decamethylcyclopentasiloxane, methylhydrogenpolysiloxane, highly polymerized methylpolysiloxane, silicone resins, amino-modified silicones, alkyl-modified silicones and the like. Examples of the other types of the liquid oils include organic UV absorbers, such as 2-ethylhexyl 4-methoxycinnamate, butylmethoxydibenzoylmethane, 2-ethylhexyl dimethoxybenzylidene dioxoimidazolidine propionate and the like. The liquid oil may contain only one material or may contain a plurality of materials. The content of the liquid oil in the oil component is preferably 10 to 99 mass %, more preferably 20 to 95 mass %.

The liquid perfumes may be conventionally-employed and commonly-known perfumes. The liquid perfume may contain only one material or may contain a plurality of materials. The content of the liquid perfume in the oil component is preferably 10 to 99 mass %, more preferably 20 to 95 mass %.

Among these, the liquid oil more preferably contains liquid silicones, which are liquid oils.

In the hydrogel particles of this embodiment, each disperse phase portion contains titanium oxide particles dispersed therein, which have a UV-shielding property.

In terms of UV-shielding property, the content of the titanium oxide particles in the disperse phase portion is preferably 5 to 60 mass %, more preferably 10 to 60 mass %, and even more preferably 10 to 50 mass %. In terms of UV-shielding property, the total content of the titanium oxide particles in the hydrogel particle is preferably 0.1 to 40 mass %, more preferably 1 to 40 mass %, and even more preferably 1 to 30 mass %.

Titanium oxide particles have a UV-shielding property. The phrase "having UV-shielding property" means having the effect of absorbing or scattering ultraviolet light with a wavelength within the range of 280 to 400 nm, especially UVB and UVAII with a wavelength within the range of 280 to 340 nm.

In terms of feel of products when applied, the average particle diameter of primary particles of the titanium oxide particles is preferably 0.001 µm or more, more preferably 0.005 µm or more, and even more preferably 0.01 µm or more. In terms of transparency of cosmetic products when applied, the average particle diameter of primary particles of the titanium oxide particles is preferably 0.1 µm or less, more preferably 0.08 µm or less, and even more preferably 0.06 µm or less. The average particle diameter is represented by the number average value of particle diameters measured by electron micrograph observation unless otherwise specified.

The titanium oxide particle may be one whose particle surface has not been subjected to a surface activity suppressing treatment, or one whose particle surface has been subjected to the surface activity suppressing treatment, so that a surface activity suppressing agent which suppresses surface activity is adhered to the particle surface. Examples of the surface activity suppressing agent include aluminum hydroxide (or alumina), hydrous silicic acid, silicones (silicone oils, such as polymethylhydrosiloxane, polydimethylsiloxane, polymethylphenylsiloxane and the like; alkylsilanes, such as methyltrimethoxysilane, ethyltrimethoxysilane, hexyltrimethoxysilane, octyltrimethoxysilane and the like; and fluoroalkylsilanes, such as trifluoromethylethyltrimethoxysilane, heptadecafluorodecyltrimethoxysilane and the like), fatty acids (palmitic acid, isostearic acid, stearic acid, lauric acid, myristic acid, behenic acid, oleic acid, rosin acid, 1,2-hydroxystearic acid, etc.), fatty acid soaps (aluminum stearate, calcium stearate, 1,2-hydroxystearic acid, etc.), fatty acid esters (dextrin fatty acid esters, cholesterol fatty acid esters, sucrose fatty acid esters, starch fatty acid esters, etc.), and the like. The particle surface of the titanium oxide particle is preferably previously subjected to the surface activity suppressing treatment which is a silicone treatment.

Incidentally, in a cosmetic product or the like which contains an ionic water-soluble polymer compound, such as a carboxyvinyl polymer, an alkyl-modified carboxyvinyl polymer or the like, as a thickening agent, it may be difficult to appropriately control the viscosity because of interaction due to contact with ionic groups of other ingredients or other ionic substances. For example, when a UV-shielding cosmetic product contains zinc oxide particles or titanium oxide particles, a local decrease or increase in the viscosity occurs, and therefore, it is difficult to ensure the stability. This may be because the surface of the titanium oxide particles or the like are previously treated by a surface activity suppressing agent, such as aluminum hydroxide, hydrous silicic acid or the like, and when the titanium oxide particles are added to an aqueous phase which is thickened by the ionic water-soluble polymer compound, interaction between surface activity suppressing agent-derived ions and the ionic water-soluble polymer compound induces an increase or decrease in the viscosity of the cosmetic product or the like. This problem may be solved by causing the disperse phase portions to be solid phase to immobilize the zinc oxide particles therein, as described in Patent Document 3. In this case, however, a large amount of a solid oil is required to cause the disperse phase portions to be solid phase. When this technique is applied to a cosmetic product or the like, a problem arises, such as poor spreadability when being applied or a sticky feel after being applied. On the other hand, according to the hydrogel particles of this embodiment, a higher alcohol and a solid paraffin are contained as the solid oil of the oil component, the content of the solid oil in the oil component is 1 to 12 mass %, and the hydrogel particles have a volume-average particle diameter of 10 to 300 µm, and therefore, even when it is applied to a cosmetic product or the like, advantages can be obtained, such as good spreadability when being applied or a reduction in a sticky feel after being applied. In addition, if the surface activity suppressing agent is a silicone, the surface of the titanium oxide particle is treated by the silicone. Therefore, in this case, even if the surface activity suppressing agent is attached to the particle surface, an increase or decrease in the viscosity of the cosmetic product or the like due to the surface activity suppressing agent can be delayed, and therefore, the stability of the cosmetic product or the like can be sustained for a long period of time.

Also, for a reason similar to that described above, in the hydrogel particles of this embodiment, the content of the solid oil in the disperse phase portion is preferably 1 to 12 mass %, more preferably 1 to 10 mass %.

The continuous phase portion may contain, in addition to the gel source of non-crosslinked hydrogel and water, a water-soluble organic compound, such as a saccharide, a polyhydric alcohol, a water-soluble polymer compound, a water-soluble perfume or the like, which are described in Japanese Patent Publication 2000-126586.

Each of the continuous phase portion and the disperse phase portions may contain other components, such as a colorant, a preservative and the like. Examples of the colorant include pigments and dyes. Examples of the pigments include inorganic pigments, such as carbon black, iron red, titanium oxide and the like, and organic pigments, such as tar pigments and the like. Examples of the dyes include solvent dyes, vat dyes, and color lakes. Examples of the preservative include paraoxymethylbenzoate, isopropylmethylphenol, ethanol, phenoxyethanol, dehydroacetic acid, and salts thereof.

The continuous phase portion and the disperse phase portions may each contain other components applicable to cosmetic products, drugs, quasi drugs, food products and the like, such as a humectant, an antiperspirant, an antimicrobial agent, a bactericide, a powder and the like.

Moreover, the continuous phase portion and the disperse phase portions may each contain zinc oxide particles, which have a UV-shielding property. In terms of feel of products when applied, the average particle diameter of primary particles of the zinc oxide particles is preferably 0.001 µm or more, more preferably 0.005 µm or more, and even more preferably 0.01 µm or more. In terms of transparency of cosmetic products when applied, the average particle diameter of primary particles of the zinc oxide particles is preferably 0.1 µm or less, more preferably 0.08 µm or less, and even more preferably 0.06 µm or less.

The hydrogel particles of this embodiment may include, in addition to the continuous phase portion and the disperse phase portions, an oily disperse phase portions which contains an oil, such as an organic UV absorber, a feel regulator or the like, and do not contain a titanium oxide particle.

(Method for Producing Hydrogel Particles)

A method for producing the hydrogel particles of this embodiment will be described.

<Preparation of Oil-in-Water Dispersion>

Initially, for an aqueous component which is a constituent of the continuous phase portion, a gel source is mixed with ion-exchanged water, and the mixture is heated to a temperature equal to or higher than the dissolution temperature of the gel source so as to sufficiently dissolve the gel source, thereby preparing a continuous phase component solution. Meanwhile, constituents for the disperse phase portion are mixed and dissolved by heating, thereby preparing a disperse phase component solution.

Thereafter, the continuous phase component solution and the disperse phase component solution are mixed at a temperature equal to or higher than the gelation temperature to prepare an oil-in-water dispersion. The method for preparing the oil-in-water dispersion is not particularly limited. The preparation of the oil-in-water dispersion can be carried out using a known technique with any of various stirrers, dispersers and the like.

In terms of stability of the oil-in-water dispersion, an emulsifying/dispersing agent is preferably added to the continuous phase component solution and/or the disperse phase component solution. Especially preferably, the emulsifying/dispersing agent is added to the continuous phase component solution.

Examples of the emulsifying/dispersing agent include polymer emulsifying/dispersing agents, nonionic surfactants, anionic surfactants, cationic surfactants, and amphoteric surfactants. The emulsifying/dispersing agent may contain only one material or may contain a plurality of materials. In terms of smooth spreadability over the human skin of cosmetic products or the like containing the hydrogel particles and in terms of good handleability during washing of the hydrogel particles and blending of the hydrogel particles into cosmetic products or the like, it is preferable to use a nonionic surfactant, an anionic surfactant, a cationic surfactant or an amphoteric surfactant in combination with a polymer emulsifying/dispersing agent, as the emulsifying/dispersing agent. More preferably, a nonionic surfactant and a polymer emulsifying/dispersing agent are used in combination. Even more preferably, a polymer emulsifying/dispersing agent is used alone. When a polymer emulsifying/dispersing agent is used as the emulsifying/dispersing agent, addition of a surfactant can be reduced or eliminated. Therefore, stickiness of cosmetic products or the like containing the hydrogel particles which may be caused by a surfactant when applied on the human skin, can be reduced.

Examples of the polymer emulsifying/dispersing agent include synthetic polymer compounds, such as acrylic acid-alkyl methacrylate copolymers, a composite formed by a reaction of an amphoteric polymer and a higher fatty acid described in Japanese Patent Publication H7-100356, water-soluble amphiphilic polymer electrolytes described in Japanese Patent Publication H8-252447 and Japanese Patent Publication H9-141079, water-soluble crosslinked amphiphilic polymer electrolytes described in Japanese Patent Publication H9-141080 and Japanese Patent Publication H9-141081, acrylic acid copolymers described in Japanese Patent Publication H10-53625, polysaccharide derivatives described in Japanese Patent No. 3329689 and Japanese Patent Publication H10-330401 and Japanese Patent Publication H11-106401, polyvinylpyrrolidone, polyvinyl alcohol and derivatives thereof, polyacrylamide, ethylene oxide adducts of alkylphenol-formaldehyde condensation products, and the like, and naturally-occurring polymer compounds, such as guar gum, karaya gum, tragacanth gum, gum arabic, arabinogalactan, casein, and the like.

Among the polymer emulsifying/dispersing agents, in terms of reduction in stickiness of cosmetic products or the like containing the hydrogel particles when applied on the human skin, an acrylic acid-alkyl methacrylate copolymer (e.g., PEMULEN (trade name) manufactured by Nikko Chemicals Co., Ltd., etc.), polyvinyl alcohol (e.g., GOHSENOL (trade name) manufactured by Nippon Synthetic Chemical Industry Co., Ltd., etc.), and a polysaccharide derivative described in Japanese Patent No. 3329689 are preferably used. More preferably, polyvinyl alcohol and the polysaccharide derivative described in the Japanese Patent No. 3329689 are used in combination.

In terms of improvement in emulsifiability and dispersibility, a neutralized polymer emulsifying/dispersing agent may be added. Alternatively, potassium hydroxide, sodium hydroxide or the like may be added to the continuous phase component solution and/or the disperse phase component solution before or after dispersion, whereby the polymer emulsifying/dispersing agent is neutralized. The value of pH after neutralization is preferably 4 to 8, more preferably 6 to 7.

Examples of the anionic surfactants include sodium lauryl sulfate, sodium stearate, polyoxyethylene lauryl ether sodium phosphate and the like.

Examples of the cationic surfactants include lauryl trimethyl ammonium chloride, stearylamine acetate, stearylamine acid and the like.

In terms of prevention of leakage of the oil component from the produced hydrogel particles, the nonionic surfactant preferably has an HLB value of 10 or less, more preferably 8 or less, even more preferably 5 or less, and especially preferably 3 or less. HLB values can be determined based on a formula described in "Techniques of Emulsification and Solubilization" published by Kougakutosho Ltd. (May 2, 1984), pp. 8-12.

Among such nonionic surfactants, in terms of less skin irritation caused by cosmetic products or the like containing the produced hydrogel particles, sorbitan fatty acid esters, polyoxyethylene sorbitan fatty acid esters, and polyoxyethylene sorbitol fatty acid esters are preferably used. More preferably, sorbitan monostearate is used. In terms of prevention of leakage of the oil component from the produced hydrogel particles, the melting point of the nonionic surfactant used is preferably 35° C. or more, more preferably 40 to 90° C., even more preferably 50 to 90° C., and especially preferably 60 to 80° C.

Examples of the amphoteric surfactants include alkydimethylaminoacetic acid betaine, lecithin and the like.

<Particle Formation of Oil-in-Water Dispersion>

Next, after preparation of the oil-in-water dispersion, the hydrogel particles are produced from the oil-in-water dispersion using a commonly-employed dropping, spraying or stirring method. It should be noted that, in terms of suppression of leakage of the oil component from the hydrogel particles, the dropping or spraying method is more preferably used than the stirring method.

The dropping method utilizes a phenomenon that an oil-in-water dispersion ejected through an orifice forms droplets by the surface or interfacial tension. The droplets are cooled in a gas phase (e.g., air) or liquid phase to solidify into hydrogel particles. In terms of production of hydrogel particles having a uniform particle diameter, the oil-in-water dispersion ejected through the orifice is preferably vibrated.

The spraying method uses a spray nozzle through which a dispersion is sprayed into a gas phase, whereby droplets of the dispersion are formed by the surface tension. The droplets are cooled in a gas phase to solidify into hydrogel particles.

In the stirring method, an oil-in-water dispersion is poured into a solution which has the property of being substantially unmixable with the oil-in-water dispersion and which is adjusted to a temperature equal to or higher than the gelation temperature. The solution is stirred to atomize the oil-in-water dispersion by the shearing force of stirring, whereby droplets are formed by the surface tension. The droplets are cooled in a liquid which is substantially unmixable with the oil-in-water dispersion to solidify into hydrogel particles.

In any of the dropping method, the spraying method and the stirring method, the temperature of the oil-in-water dispersion when ejected, sprayed or poured is preferably between the gelation temperature and 100° C. In terms of readily production of spherical particles with excellent aesthetic appearance, the temperature of the oil-in-water dispersion is preferably higher than the gelation temperature by 10° C. or more, more preferably higher than the gelation temperature by 20° C. or more. It should be noted that the upper limit of this temperature is the boiling point of water, i.e., 100° C.

The hydrogel particles thus produced may be processed into finer hydrogel particles by crushing or any other means as necessary.

<UV-Shielding Cosmetic Products>

Moreover, a cosmetic product having a UV-shielding property can be obtained by adding the hydrogel particles. In this case, the hydrogel particles are applicable to both w/o and o/w type cosmetic products. Particularly, o/w type cosmetic products are preferable.

The content of the hydrogel particles in the UV-shielding cosmetic product is preferably 5 to 80 mass %, more preferably 10 to 75 mass %. The content of titanium oxide particles in the UV-shielding cosmetic product is preferably 0.1 to 20 mass %, more preferably 1 to 10 mass %.

The UV absorbing effect of UV-shielding cosmetic products can be enhanced by further adding an organic UV absorber. The organic UV absorber used in this case is not particularly limited. Any of both oil- and water-soluble organic UV absorbers can be preferably used, e.g., those described in Japanese Patent Publication 2006-225311. Examples of the oil-soluble organic UV absorbers include those based on benzoic acid, salicylic acid, cinnamic acid, and benzophenone.

The content of the organic UV absorber in the UV-shielding cosmetic product is preferably 1 to 20 mass %, more preferably 2 to 10 mass %, in terms of absence of stickiness on the human skin and effect of absorbing ultraviolet light.

The UV-shielding cosmetic products can contain an oil for adjustment of a feel. An example of the oil is one which is described in Japanese Patent Publication 2006-225311. Particularly, the oil is preferably an ester oil or a silicone oil in terms of improvement in a feel. The content of the oil in the UV-shielding cosmetic product is preferably 0.1 to 10 mass %, more preferably 0.1 to 5 mass %.

A surfactant, a skin whitening agent, a bactericide, an antiperspirant, a humectant, a cooling agent, a perfume, a colorant and the like can be added to the UV-shielding cosmetic products in addition to the aforementioned ingredients, as long as the advantages of the present invention are not impaired.

By applying the UV-shielding cosmetic products to the human skin, stickiness or dryness of the human skin is suppressed, and moreover, the feel is sustained so that an effective ingredient of the UV absorber or the like can be caused to remain in the human skin for a long period of time.

EXAMPLES (Hydrogel Particles)

Hydrogel particles according to Examples 1 to 4 and Comparative Examples 1 to 3 were prepared. The composition of each of the hydrogel particles is also shown in Table 1.

Example 1

A disperse phase component solution was prepared which contains a higher alcohol (KALCOL 220-80 (trade name)

manufactured by Kao Corporation, melting point: 72° C., a mixture of those with 18 to 22 carbon atoms, behenyl alcohol content: 80 mass % or more) and a solid paraffin (Multiwax 835 (trade name) manufactured by SONNEBORN) as solid oils, polyglycerin-modified silicone (KF-6104 (trade name) manufactured by Shin-Etsu Chemical Co., Ltd.) and cyclopentasiloxane (KF-995 (trade name) manufactured by Shin-Etsu Chemical Co., Ltd., melting point: −40° C.) as liquid oils (the solid and liquid oils are an oil component), and hydrophobized fine titanium oxide particles (surface-treated by silicone serving as a surface activity suppressing agent). In this case, the contents of the constituents of the final hydrogel particle were as follows: the higher alcohol 1.0 mass %; the solid paraffin 1.0 mass %; the polyglycerin-modified silicone 2.45 mass %; the cyclopentasiloxane 20.3 mass %; and the hydrophobized fine titanium oxide particles 12.25 mass %. The contents of the constituents of the disperse phase component solution were as follows: the higher alcohol 2.70 mass %; the solid paraffin 2.70 mass %; the polyglycerin-modified silicone 6.62 mass %; the cyclopentasiloxane 54.9 mass %; and the hydrophobized fine titanium oxide particles 33.1 mass %. Therefore, the solid oil content of the disperse phase component solution was 5.4 mass %. The solid oil content of the oil component was 8.08 mass %.

A continuous phase component (aqueous component) solution was prepared which contains agar (UP-16 (trade name) manufactured by Ina Food Industry, Co., Ltd., jelly strength: 58.8 kPa), polyvinyl alcohol (GOHSENOL EG-05 (trade name) manufactured by Nippon Synthetic Chemical Industry Co., Ltd.), a polysaccharide derivative (SPS-S (trade name) manufactured by Kao Corporation, hydroxyethyl cellulose hydroxypropylstearyl ether hydroxypropyl sodium sulfonate), and purified water. In this case, the contents of the constituents of the final hydrogel particle were as follows: the agar 1.0 mass %; the polyvinyl alcohol 0.5 mass %; the polysaccharide derivative 0.1 mass %; and the balance is the purified water.

The disperse phase component solution and the continuous phase component solution were prepared in a total amount of 3,000 g, where their mass ratio is 37:63. The disperse phase component solution was melted by heating at 80° C. and the continuous phase component solution was dissolved by heating at 90° C. Thereafter, the disperse phase component solution at 80° C. and the continuous phase component solution cooled to 80° C. were mixed by stirring using an anchor stirrer to obtain a mixture liquid thereof.

Next, the mixture liquid was stirred for three minutes using an emulsifier (T.K. HOMO MIXER MARK II Model 2.5 (trade name) manufactured by Tokushu Kika Kogyo Kabushiki Kaisha) at 10,000 rpm to prepare an oil-in-water dispersion.

Thereafter, the oil-in-water dispersion was heated to 80° C. The oil-in-water dispersion was sprayed into a 500-L tank cooled at 10° C., at a flow rate of 10 kg/hr, using a spray nozzle (SUE-28B (trade name) manufactured by Spraying Systems Co.), where the gas to liquid ratio (gas/liquid) was 1063. Hydrogel particles which are liquid drops of the dispersion which were formed by spraying and were then solidified by cooling, were recovered from a lower portion of the tank. The hydrogel particles are of Example 1. The hydrogel particles of Example 1 had a volume-average particle diameter of 61 μm. Note that the volume-average particle diameter was measured by a laser diffraction/scattering method using a laser diffraction/scattering particle size distribution analyzer (e.g., Model No. LA-910 manufactured by HORIBA, Ltd.).

Example 2

Hydrogel particles were prepared which had the same composition as that of Example 1, except that Multiwax 445 (trade name) manufactured by SONNEBORN was used as a solid paraffin. The hydrogel particles are of Example 2. The hydrogel particles of Example 2 had a volume-average particle diameter of 87 μm.

Example 3

Hydrogel particles were prepared which had the same composition as that of Example 1, except that HiMic 1045 (trade name) manufactured by NIPPON SEIRO CO., LTD. was used as a solid paraffin. The hydrogel particles are of Example 3. The hydrogel particles of Example 3 had a volume-average particle diameter of 61 μm.

Example 4

Hydrogel particles of Example 4 were prepared in a manner similar to that of Example 3, except that the disperse phase component solution and the continuous phase component solution were mixed by stirring, where the final hydrogel particle contained 1.5 mass % of the higher alcohol and 1.5 mass % of the solid paraffin, and the mass ratio of the oil component solution and the aqueous component solution was 38:62; the mixture solution was sprayed through a spray nozzle (hollow cone spray nozzle (K-010) manufactured by H.IKEUCHI Co., Ltd.) at a flow rate of 12 kg/hr into a gas phase at 25° C., at a height of 3.4 m, while the temperature of the mixture liquid was maintained at 80° C.; and particles which were precipitated in the gas phase were collected, to obtain hydrogel particles. In the hydrogel particles of Example 4, the contents of the constituents of the disperse phase component solution were as follows: the higher alcohol 3.95 mass %; the solid paraffin 3.95 mass %; the polyglycerin-modified silicone 6.45 mass %; the cyclopentasiloxane 53.4 mass %; and the hydrophobized fine titanium oxide particles 32.2 mass %. Therefore, the solid oil content of the disperse phase component solution was 7.9 mass %. The solid oil content of the oil component was 11.7 mass %. The hydrogel particles of Example 4 had a volume-average particle diameter of 220 μm.

Comparative Example 1

Hydrogel particles having the same composition as that of Example 3 were prepared, except that the disperse phase component solution and the continuous phase component solution were mixed by stirring, where the final hydrogel particle contained 2.5 mass % of the higher alcohol and 2.5 mass % of the solid paraffin, and the mass ratio of the disperse phase component solution and the continuous phase component solution was 40:60. The hydrogel particles are of Comparative Example 1. In the hydrogel particles of Comparative Example 1, the contents of the constituents in the disperse phase component solution were as follows: the higher alcohol 6.25 mass %; the solid paraffin 6.25 mass %; the polyglycerin-modified silicone 6.13 mass %; the cyclopentasiloxane 50.8 mass %; and the hydrophobized fine titanium oxide particles 30.6 mass %. Therefore, the solid oil content of the disperse phase component solution was 12.5 mass %. The solid oil content of the oil component was 18.0 mass %. The hydrogel particles of Comparative Example 1 had a volume-average particle diameter of 56 μm.

Comparative Example 2

Hydrogel particles having the same composition as that of Example 1 were prepared, except that the disperse phase component solution and the continuous phase component solution were mixed by stirring, where the solid oil did not contain a solid paraffin, the final hydrogel particle contained 3.0 mass % of the higher alcohol, and the mass ratio of the disperse phase component solution and the continuous phase component solution was 38:62. The hydrogel particles are of Comparative Example 2. In the hydrogel particles of Comparative Example 2, the contents of the constituents of the disperse phase component solution were as follows: the higher alcohol 7.89 mass %; the polyglycerin-modified silicone 6.45 mass %; the cyclopentasiloxane 53.4 mass %; and the hydrophobized fine titanium oxide particles 32.2 mass %. Therefore, the solid oil content of the disperse phase component solution was 7.9 mass %. The solid oil content of the oil component was 11.7 mass %. The hydrogel particles of Comparative Example 2 had a volume-average particle diameter of 58 μm.

Comparative Example 3

Hydrogel particles having the same composition as that of Example 1 were prepared, except that the oil component solution and the aqueous component solution were mixed by stirring, where the solid oil did not contain a higher alcohol, and the final hydrogel particle contained 2.0 mass % of the solid paraffin. The hydrogel particles are of Comparative Example 3. In the hydrogel particles of Comparative Example 3, the contents of the constituents of the disperse phase component solution were as follows: the solid paraffin 5.41 mass %; the polyglycerin-modified silicone 6.62 mass %; the cyclopentasiloxane 54.9 mass %; and the hydrophobized fine titanium oxide particles 33.1 mass %. Therefore, the solid oil content of the disperse phase component solution was 5.4 mass %. The solid oil content of the oil component was 8.08 mass %. The hydrogel particles of Comparative Example 3 had a volume-average particle diameter of 100 μm.

Comparative Example 4

A disperse phase component solution and a continuous phase component solution having compositions similar to those of Example 1 were prepared in a total amount of 300 g, where the mass ratio of the disperse phase component solution and a continuous phase component solution was 37:63. The disperse phase component solution was melted by heating at 80° C. and the continuous phase component solution was dissolved by heating at 90° C. Thereafter, the disperse phase component solution at 80° C. and the continuous phase component solution cooled to 80° C. were mixed by stirring using an anchor stirrer to obtain a mixture liquid thereof.

Next, the mixture liquid was stirred for one minute using an emulsifier (T.K. HOMO MIXER MARK II Model 2.5 (trade name) manufactured by Tokushu Kika Kogyo Kabushiki Kaisha) at 10,000 rpm to prepare an oil-in-water dispersion.

Thereafter, a silicone oil (KF-96A20CS (trade name) manufactured by Shin-Etsu Chemical Co., Ltd.) in which 0.1 mass % of polyether silicone (KF-6013 (trade name) manufactured by Shin-Etsu Chemical Co., Ltd.) was dissolved was heated to 70° C. Thereafter, the previously prepared mixture liquid was dropped into the silicone oil kept at 70° C. at a rate of 100 g/min. Note that the dropping was carried out while stirring the silicone oil using an anchor blade.

After the mixture solution was completely dropped, the silicone oil was cooled to 10° C. to allow the mixture liquid dispersed in the silicone oil to solidify by cooling, so that hydrogel particles were obtained. Note that the cooling was carried out while stirring the silicone oil using an anchor blade. The hydrogel particles are of Comparative Example 4. The hydrogel particles of Comparative Example 4 had a volume-average particle diameter of 400 μm.

TABLE 1

| | | | | | Example | | | | Comparative Example | | | |
|---|---|---|---|---|---|---|---|---|---|---|---|---|
| | | | | | 1 | 2 | 3 | 4 | 1 | 2 | 3 | 4 |
| Composition of hydrogel particle mass % | Disperse phase | Oil component | Solid oil | Higher alcohol manufactured by Kao Corporation Trade name: KALCOL 220-80 | 1.0 | 1.0 | 1.0 | 1.5 | 2.5 | 3.0 | | 1.0 |
| | | | | Solid paraffin manufactured by NIPPON SEIRO CO., LTD. Trade name: HiMic 1045 | | | 1.0 | 1.5 | | | | |
| | | | | Solid paraffin manufactured by SONNEBORN Trade name: Multiwax 445 | | 1.0 | | | | | | |
| | | | | Solid paraffin manufactured by SONNEBORN Trade name: Multiwax 835 | 1.0 | | | | | | | |
| | | | Liquid oil | Polyglycerin-modified silicone manufactured by Shin-Etsu Chemical Co., Ltd. Trade name: KF-6104 | 2.45 | 2.45 | 2.45 | 2.45 | | | | |
| | | | | Cyclopentasiloxane manufactured by Shin-Etsu Chemical Co., Ltd. Trade name: KF-995 | 20.3 | 20.3 | 20.3 | 20.3 | | | | |
| | | | | Hydrophobized fine titanium oxide particles | 12.25 | 12.25 | 12.25 | 12.25 | | | | |
| | Continuous phase • Aqueous component | | | Agar manufactured by Ina Food Industry, Co., Ltd. Trade name: UP-16 | 1.0 | 1.0 | 1.0 | 1.0 | | | | |
| | | | | Polyvinyl alcohol manufactured by Nippon Synthetic Chemical Industry Co., Ltd. Trade name: GOHSENOL EG-05 | 0.5 | 0.5 | 0.5 | 0.5 | | | | |
| | | | | Polysaccharide derivative manufactured by Kao Corporation Trade name: SPS-S | 0.1 | 0.1 | 0.1 | 0.1 | | | | |
| | | | | Purified water | balance | balance | balance | balance | | | | |
| Solid oil content of disperse phase portion (mass %) | | | | | 5.4 | 5.4 | 5.4 | 7.9 | | | | |
| Solid oil content of oil component (mass %) | | | | | 8.08 | 8.08 | 8.08 | 11.7 | | | | |
| Volume-average particle diameter of hydrogel particles (μm) | | | | | 61 | 87 | 61 | 220 | | | | |

TABLE 1-continued

| particle mass % | | | Solid paraffin manufactured by NIPPON SEIRO CO., LTD. Trade name: HiMic 1045 | 2.5 | | | |
|---|---|---|---|---|---|---|---|
| | | | Solid paraffin manufactured by SONNEBORN Trade name: Multiwax 445 | | | | |
| | | | Solid paraffin manufactured by SONNEBORN Trade name: Multiwax 835 | | | 2.0 | 1.0 |
| | | Liquid oil | Polyglycerin-modified silicone manufactured by Shin-Etsu Chemical Co., Ltd. Trade name: KF-6104 | 2.45 | 2.45 | 2.45 | 2.45 |
| | | | Cyclopentasiloxane manufactured by Shin-Etsu Chemical Co., Ltd. Trade name: KF-995 | 20.3 | 20.3 | 20.3 | 20.3 |
| | | | Hydrophobized fine titanium oxide particles | 12.25 | 12.25 | 12.25 | 12.25 |
| | Continuous phase Aqueous component | | Agar manufactured by Ina Food Industry, Co., Ltd. Trade name: UP-16 | 1.0 | 1.0 | 1.0 | 1.0 |
| | | | Polyvinyl alcohol manufactured by Nippon Synthetic Chemical Industry Co., Ltd. Trade name: GOHSENOL EG-05 | 0.5 | 0.5 | 0.5 | 0.5 |
| | | | Polysaccharide derivative manufactured by Kao Corporation Trade name: SPS-S | 0.1 | 0.1 | 0.1 | 0.1 |
| | | | Purified water | balance | balance | balance | balance |
| Solid oil content of disperse phase portion (mass %) | | | | 12.5 | 7.9 | 5.4 | 5.4 |
| Solid oil content of oil component (mass %) | | | | 18.0 | 11.7 | 8.08 | 8.08 |
| Volume-average particle diameter of hydrogel particles (μm) | | | | 56 | 58 | 100 | 400 |

(Testing and Evaluation Method)

An acrylic acid-alkyl methacrylate copolymer (e.g., PEMULEN TR-2 (trade name) manufactured by Nikko Chemicals Co., Ltd.), 2-ethylhexyl 4-methoxycinnamate (Uvinul MC-80 (trade name) manufactured by BASF Corporation), ethylene glycol monophenyl ether (High-solve EPH (trade name) manufactured by TOHO Chemical Industry Co., LTD.), a 48% potassium hydroxide solution (Liquid caustic potash (48%) (trade name) manufactured by TOAGOSEI CO., LTD.), ethanol (95% synthetic alcohol (trade name) manufactured by JAPAN SYNTHETIC ALCOHOL CO., LTD.), and purified water were mixed to prepare a cosmetic base. In this case, the contents of the constituents of the final cosmetic product were as follows: the acrylic acid-alkyl methacrylate copolymer 0.20 mass %; the 2-ethylhexyl 4-methoxycinnamate 8.50 mass %; the ethylene glycol monophenyl ether 0.40 mass %; the potassium hydroxide solution (48%) 0.20 mass %, the ethanol 7.0 mass %; and the balance is the purified water.

In order to study the appropriateness of application to sunscreen gel, each of the hydrogel particles of Examples 1 to 4 and Comparative Examples 1 to 3 was mixed with the aforementioned cosmetic base at the ratio of 1:1 to prepare a UV-shielding cosmetic product. Each composition is shown in Table 2.

TABLE 2

| | | Example | | | | Comparative Example | | | |
|---|---|---|---|---|---|---|---|---|---|
| | | 1 | 2 | 3 | 4 | 1 | 2 | 3 | 4 |
| Components of cosmetic product mass % | Acrylic acid-alkyl methacrylate copolymer manufactured by Nikko Chemicals Co., Ltd. Trade name: PEMULEN TR-2 | 0.20 | 0.20 | 0.20 | 0.20 | 0.20 | 0.20 | 0.20 | 0.20 |
| | 2-ethylhexyl 4-methoxycinnamate manufactured by BASF Corporation Trade name: Uvinul MC-80 | 8.50 | 8.50 | 8.50 | 8.50 | 8.50 | 8.50 | 8.50 | 8.50 |
| | Ethylene glycol monophenyl ether manufactured by TOHO Chemical Industry Co., LTD. Trade name: High-solve EPH | 0.40 | 0.40 | 0.40 | 0.40 | 0.40 | 0.40 | 0.40 | 0.40 |
| | Potassium hydroxide solution (48%) manufactured by TOAGOSEI CO., LTD. Trade name: Liquid caustic potash (48%) | 0.20 | 0.20 | 0.20 | 0.20 | 0.20 | 0.20 | 0.20 | 0.20 |
| | Ethanol manufactured by JAPAN SYNTHETIC ALCOHOL CO., LTD. Trade name: 95% synthetic alcohol | 7.00 | 7.00 | 7.00 | 7.00 | 7.00 | 7.00 | 7.00 | 7.00 |
| | Hydrogel particles | 50.0 | 50.0 | 50.0 | 50.0 | 50.0 | 50.0 | 50.0 | 50.0 |
| | Purified water | balance | balance | balance | balance | balance | balance | balance | balance |
| Actual use test | Moistness of human skin | 4 | 4 | 4 | 3 | 1 | 2 | 1 | 1 |
| | Smoothness of human skin | 4 | 4 | 4 | 3 | 1 | 2 | 1 | 1 |
| | Sustainability of moistness of human skin | 4 | 4 | 4 | 3 | 2 | 1 | 2 | 2 |
| | Overall average score | A | A | A | B | D | C | D | D |
| | Stability test | A | A | A | A | A | B | B | A |

<Actual Use Test>

The UV-shielding cosmetic products prepared from Examples 1 to 4 and Comparative Examples 1 to 4 were applied to a forearm to carry out an actual use test for five expert panelists. Evaluation was carried out in terms of three check items: moistness of the human skin; smoothness of the human skin; and sustainability of moistness of the human skin in accordance with the following criteria. For each of the three check items, an average score was calculated from evaluations of the five experts panelists based on the following criteria. Also, an overall average score was calculated by averaging the average scores of the three check items.

—Check Items and Criteria—

Moistness of Human Skin

Score 4: moist

Score 3: slightly moist

Score 2: slightly not moist
Score 1: not moist
Smoothness of Human Skin
Score 4: smooth
Score 3: slightly smooth
Score 2: slightly not smooth
Score 1: not smooth
Sustainability of Moistness of Human Skin (One Hour after Application)
Score 4: moistness lasts
Score 3: moistness slightly lasts
Score 2: moistness does not last long
Score 1: moistness does not last
—Criteria—
Overall average score 3.5 to 4.0: A
Overall average score 2.5 to 3.4: B
Overall average score 1.5 to 2.4: C
Overall average score 1.0 to 1.4: D
<Stability Test>
UV-shielding cosmetic products prepared from Examples 1 to 4 and Comparative Examples 1 to 3 were tested in terms of presence or absence of separation immediately after preparation and after one month of preservation in atmosphere at 50° C., and were evaluated based on the following criteria.
A: good (absence of separation)
B: poor (presence of separation)
(Results of Testing and Evaluation)
Table 2 shows the results of testing and evaluation.

According to Table 2, for the moistness of the human skin, Example 1 scored 4, Example 2 scored 4, Example 3 scored 4, and Example 4 scored 3, and Comparative Example 1 scored 1, Comparative Example 2 scored 2, Comparative Example 3 scored 1, and Comparative Example 4 scored 1.

For the smoothness of the human skin, Example 1 scored 4, Example 2 scored 4, Example 3 scored 4, and Example 4 scored 3, and Comparative Example 1 scored 1, Comparative Example 2 scored 2, Comparative Example 3 scored 1, and Comparative Example 4 scored 1.

For the sustainability of the moistness of the human skin, Example 1 scored 4, Example 2 scored 4, Example 3 scored 4, and Example 4 scored 3, and Comparative Example 1 scored 2, Comparative Example 2 scored 1, Comparative Example 3 scored 2, and Comparative Example 4 scored 2.

For the overall average score of the actual use test, Example 1 scored A, Example 2 scored A, Example 3 scored A, and Example 4 scored B, and Comparative Example 1 scored D, Comparative Example 2 scored C, Comparative Example 3 scored D, and Comparative Example 4 scored D.

In the stability test, Example 1 scored A, Example 2 scored A, Example 3 scored A, and Example 4 scored A, and Comparative Example 1 scored A, Comparative Example 2 scored B, Comparative Example 3 scored B, and Comparative Example 4 scored A.

According to the results, Examples 1 to 4 had good results in both of the actual use test and the stability test. On the other hand, Comparative Example 1 which contains a large amount of a higher alcohol and a solid paraffin, Comparative Example 2 which does not contain a solid paraffin, Comparative Example 3 which does not contain a higher alcohol, and Comparative Example 4 which has a volume-average particle diameter exceeding 300 µm, all had poor results in one or both of the actual use test and the stability test.

INDUSTRIAL APPLICABILITY

The present invention is useful for hydrogel particles in which disperse phase portions containing an oil component are dispersed in a continuous phase portion of non-crosslinked hydrogel, and UV-shielding cosmetic products containing the hydrogel particles.

The invention claimed is:

1. Hydrogel particles, comprising:
a continuous phase portion of non-crosslinked hydrogel; and
at least one disperse phase portion dispersed in said continuous phase portion;
wherein each of said at least one disperse phase portion comprises a solid oil and a liquid oil as an oil component, and titanium oxide particles dispersed therein;
said solid oil of said oil component comprises behenyl alcohol and a solid paraffin, and the concentration of said solid oil in said oil component is 4 to 12 mass %;
the concentration of behenyl alcohol in said oil component is 2 to 6 mass %;
the total concentration of solid paraffin in said oil component is 2 to 6 mass %;
the concentration of said titanium oxide particles in said disperse phase portion is 5 to 50 mass %;
the total concentration of solid oil in said disperse phase portion is 1 to 12 mass %;
the total concentration of liquid oil in said disperse phase portion is 50 to 80 mass %; and
said hydrogel particles have a volume-average particle diameter of 10 to 300 µm.

2. The hydrogel particles of claim 1, wherein said titanium oxide particles have a particle surface which has been subjected to a surface activity suppressing treatment.

3. The hydrogel particles of claim 2, wherein said surface activity suppressing treatment is a silicone treatment.

4. The hydrogel particles of claim 1, wherein said liquid oil comprised in said oil component has a melting point of less than 35° C.

5. The hydrogel particles of claim 1, wherein said liquid oil comprises a silicone.

6. A UV-shielding cosmetic product, comprising hydrogel particles of claim 1.

7. The hydrogel particles of claim 2, wherein said liquid oil comprised in said oil component has a melting point of less than 35° C.

8. The hydrogel particles of claim 3, wherein said liquid oil comprised in said oil component has a melting point of less than 35° C.

9. The hydrogel particles of claim 2, wherein said liquid oil comprises a silicone.

10. The hydrogel particles of claim 3, wherein said liquid oil comprises a silicone.

11. The hydrogel particles of claim 4, wherein said liquid oil comprises a silicone.

12. The hydrogel particles of claim 7, wherein said liquid oil comprises a silicone.

13. The hydrogel particles of claim 8, wherein said liquid oil comprises a silicone.

* * * * *